(12) United States Patent
Boussey

(10) Patent No.: US 12,194,323 B2
(45) Date of Patent: Jan. 14, 2025

(54) DECORATIVE RESPIRATOR AND COMMUNICATION MASK

(71) Applicant: Riley Boussey, Waterloo (CA)

(72) Inventor: Riley Boussey, Waterloo (CA)

( * ) Notice: Subject to any disclaimer, the term of this patent is extended or adjusted under 35 U.S.C. 154(b) by 834 days.

(21) Appl. No.: 17/350,200

(22) Filed: Jun. 17, 2021

(65) Prior Publication Data

US 2022/0401762 A1    Dec. 22, 2022

(51) Int. Cl.

| | | |
|---|---|---|
| *A62B 18/08* | (2006.01) | |
| *A41D 13/11* | (2006.01) | |
| *A61F 9/02* | (2006.01) | |
| *A62B 18/02* | (2006.01) | |
| *A62B 18/04* | (2006.01) | |
| *A62B 23/02* | (2006.01) | |
| *H04B 1/3827* | (2015.01) | |
| *H04R 1/02* | (2006.01) | |

(Continued)

(52) U.S. Cl.
CPC ............. *A62B 18/08* (2013.01); *A41D 13/11* (2013.01); *A61F 9/022* (2013.01); *A62B 18/025* (2013.01); *A62B 18/04* (2013.01); *A62B 18/082* (2013.01); *A62B 18/084* (2013.01); *A62B 23/025* (2013.01); *H04B 1/385* (2013.01); *H04R 1/028* (2013.01); *H04R 1/08* (2013.01); *H04R 3/00* (2013.01); *A61F 2009/021* (2013.01); *A62B 18/086* (2013.01); *H04B 2001/3866* (2013.01); *H04R 2420/07* (2013.01)

(58) Field of Classification Search
CPC ..... A62B 18/025; A62B 18/084; A62B 23/02; A62B 18/02; A42B 3/288; A41D 13/11; A41D 13/1161; B63C 11/12; B63C 2011/126

See application file for complete search history.

(56) References Cited

U.S. PATENT DOCUMENTS

| | | | |
|---|---|---|---|
| 4,817,596 A | | 4/1989 | Gallet |
| 4,850,346 A | * | 7/1989 | Michel .................. A62B 18/10 128/206.17 |
| 5,758,639 A | | 6/1998 | Ikonen |

(Continued)

FOREIGN PATENT DOCUMENTS

| | | |
|---|---|---|
| CA | 2520480 C | 10/2004 |
| DE | 102013011195 A1 | 1/2015 |

(Continued)

*Primary Examiner* — Brandy S Lee
*Assistant Examiner* — Mishal Zahra Hussain
(74) *Attorney, Agent, or Firm* — Jordan Sworen; Daniel Enea; Argus Intellectual Enterprise, LLC

(57) ABSTRACT

A face mask is provided. The face mask comprises a decorative skin with a strap attached to an outer perimeter of the decorative skin. A respirator is attached to a connection piece and utilizes a filter. A speaker and a microphone are mounted to the face mask, and an electronic transceiver module is attached to the face mask. The strap secures the face mask to a head of the user such that an air-tight seal is formed in a worn position. The power source powers the speaker, the microphone, and the electronic transceiver module. The electronic transceiver module comprises a processor coupled to a computer memory and non-transitory computer readable media. The processor is configured to transmit and receive signals from the electronic transceiver module and the speaker or microphone.

17 Claims, 15 Drawing Sheets

(51) Int. Cl.
    *H04R 1/08*    (2006.01)
    *H04R 3/00*    (2006.01)

(56) References Cited

U.S. PATENT DOCUMENTS

| | | | |
|---|---|---|---|
| 6,101,636 A * | 8/2000 | Williams | A42B 3/0406 |
| | | | 2/410 |
| D487,534 S | 3/2004 | Broersma | |
| 8,688,040 B2 | 4/2014 | Jung | |
| 9,517,366 B2 * | 12/2016 | Kihlberg | G10L 21/0316 |
| 10,363,441 B2 * | 7/2019 | Bergeron | A62B 23/025 |
| 10,843,015 B2 | 11/2020 | Patil et al. | |
| 2008/0023002 A1 * | 1/2008 | Guelzow | A62B 18/08 |
| | | | 2/5 |
| 2009/0113590 A1 * | 5/2009 | Lian | A63B 71/10 |
| | | | 2/9 |
| 2012/0190315 A1 | 7/2012 | Glezerman et al. | |
| 2014/0245524 A1 * | 9/2014 | Stephens | A42B 3/20 |
| | | | 2/9 |
| 2016/0008640 A1 * | 1/2016 | Teetzel | A42B 3/228 |
| | | | 128/201.19 |
| 2018/0014597 A1 * | 1/2018 | Cooke | A42B 3/042 |
| 2019/0104796 A1 * | 4/2019 | Bacinska | A42B 3/08 |
| 2021/0401105 A1 * | 12/2021 | Pachao Morbitzer | A42B 3/105 |

FOREIGN PATENT DOCUMENTS

| | | | | |
|---|---|---|---|---|
| KR | 20180017775 | * | 2/2018 | A42B 3/0406 |
| WO | 2017041411 A1 | | 3/2017 | |
| WO | WO-2021064640 A1 * | | 4/2021 | A62B 18/02 |

* cited by examiner

DECORATIVE RESPIRATOR AND COMMUNICATION MASK

FIELD OF THE INVENTION

The present disclosure relates to the field of face masks, more specifically, but not by way of limitation, more particularly to devices for improved decorative respirator and communication face masks.

BACKGROUND

Any discussion of the related art throughout the specification should in no way be considered as an admission that such related art is widely known or forms part of common general knowledge in the field.

Currently, many are wearing a variation of face masks that are simple surgical masks, cloth masks without filters, cloth masks with filters, and/or clear face shields. These face mask apparatuses are generally not very attractive and rarely provide any benefit other than the mask itself to the user.

Superior protection may be provided to a user through a respirator half face mask, or full mask, although the problem remains that these masks are generally not very interesting, do not look good in appearance, and rarely provide any benefit other than the mask itself to the user.

U.S. Pat. No. D487,534 S (Broersma) discloses a design for a goggle, helmet mask combination. Shortcomings include a lack of adequate protection from harmful particles which may be in the air, such as a respirator. The design also lacks any speaker or microphone communication and lacks signal transmission or a central computer. The described goggle, helmet mask combination also lacks versatility in both design and functionality.

U.S. Pat. No. 10,843,015 B2 (Patil et al.) discloses a system and method for completing fit tests on a respirator mask and indicating end of service life for one or more elements of the respirator mask. Shortcomings include no speaker or microphone communication, and no easy way to customize the appearance of the mask. The described electronics module is also limited and does not provide a varied functionality to the user, and instead serves primarily to monitor the fit and quality of the mask itself.

U.S. Pat. No. 9,517,366 B2 (Kihlberg) discloses a speech enhancement apparatus and respirator masks including speech enhancement apparatus, as well as methods of enhancing speech transmission for the user of a respirator mask. Shortcomings include a lack of decorative skin, and no described system to attach the mask to the user's head. The described speaker and microphone is also directed towards speech enhancement, and not towards external communication.

U.S. Pat. No. 8,688,040 B2 (Jung) discloses a Bluetooth® headset for a helmet having an inter-communication. Shortcomings include a lack of respirator and any form of filtration. The described headset serves primarily as a user mounted headset, added to the user's helmet, and is not custom made for the specific helmet.

U.S. Pat. No. 6,101,636 A (Williams) discloses a helmet, preferably a motorcycle helmet, having a latex or rubbery three dimensional sculpture generally following the contour of the helmet adhered to the outer surface thereof. Shortcomings include a lack of any speaker or microphone communication, and a lack of signal transmission or central computer. The described helmet sculpture is an external addition to an existing helmet, and the application is directed towards motorcycle helmets which typically lack respirators or filtration devices.

U.S. Pat. No. 5,758,639 A (Ikonen) discloses a combination of a helmet or a protective mask and a respirator that can function under ram pressure. Shortcomings include a lack of speaker and microphone communication, and a lack of signal transmission or central computer. The described helmet also lacks versatility in both design and functionality.

U.S. Pat. No. 4,817,596 A (Gallet) discloses a helmet that is specifically usable in combination with a respirator mask. Shortcomings include a lack of speaker and microphone communication, and a lack of signal transmission or central computer.

U.S. Pub. No. 2012/0190315 A1 (Glezerman et al.) discloses a communications system that is configured to attach to a helmet that includes vent openings formed in an outer shell of the helmet. The system can include a main communications module and the system can further include other audio components that include speakers and a microphone. Shortcomings include a lack of protection from a respirator or any form a filtration. The described communications system is also an external attachment to an existing helmet, and not built into the helmet. The described communications system also lacks any decorative nature and lacks versatile design features.

W.O. Pub. No. 2017/041411 A1 (Feng) discloses a motorcycle helmet Bluetooth® device comprising a server, a power supply, an adjustment component, a microphone and an earpiece. Shortcomings include a lack of protection from a respirator or filtration system. The described Bluetooth® device is also an attachment to an existing helmet, and not built into the helmet. The described communications system also lacks any decorative nature and lacks versatile design features.

D.E. Pub. No. 10 2013 011 195 A1 (Krüger et al.) discloses a personal protection system for emergency services that allows communication with helmet and with or without respirator. The invention further relates to a helmet and a respiratory mask and a method for controlling a communication of a personal protection system. Shortcomings include the lack of versatility of the described system, especially in terms of communication, where the system primarily targets communication between two users who are both wearing this personal protection system. There is also a lack of decorative nature with respect to the design of the mask.

C.A. Pub. No. 2 520 480 C (Farrell et al.) discloses a head protection system comprising a helmet shell, a visor mounting for pivotally mounting a visor to the shell to enable the visor to be moved between raised and lowered positions, and a retainer for releasably retaining the visor to the helmet. Shortcomings include a lack of versatile functionality with respect to the use of a speaker and microphone for communication. Further shortcomings include the lack of design and decorative nature, and the lack of a respirator and self-adjusting connection piece.

All documents cited herein are incorporated by reference.

It is clear that there exists a need for a face mask and/or helmet which provides adequate protection to the user using a respirator which is connected to the mask, maintains a proper seal against the user's face, yet is also customizable and is attractive. There is also a need for a face mask and/or helmet which has speaker and microphone communication and signal transmission, built into the mask.

Applicant proposes a decorative respirator and communication mask that overcomes disadvantages inherent in the existing respirator and face mask apparatuses, such as, but not limited to, a lack of respiratory protection, a lack of comfort and adjustability, a lack of desirable or interesting looking designs, a lack of speaker and microphone communication, a lack of wired or wireless transmission of signals, among others. The present invention provides an equally protective face mask that may be attractive and stylish in appearance and may provide additional benefit to the user through speakers and a microphone, among other benefits. As such, the general purpose of the present invention, which will be described subsequently in greater detail, is to provide a new and improved face mask respirator which provides the advantages and overcomes the aforementioned disadvantages.

BRIEF SUMMARY

It is the object of the present invention to provide a face mask. The face mask comprises a decorative appearance and communication device for a user, comprising a decorative skin with at least one strap attached to an outer perimeter of the decorative skin. A respirator that utilizes at least one filter is attached to a connection piece, wherein the connection piece is attached to the decorative skin. At least one speaker and at least one microphone are mounted to an interior of the face mask. An electronic transceiver module is attached to the face mask and a power source is attached to the face mask. The at least one strap secures the face mask to a head of the user in a worn position. The at least one filter is connected to the respirator, wherein the respirator forms an air-tight seal with a face of the user in the worn position. The power source powers the at least one speaker, the at least one microphone, and the electronic transceiver module. The processor is configured to transmit and receive signals from the electronic transceiver module and the at least one speaker or the at least one microphone.

In accordance with an embodiment of the invention, the electronic transceiver module comprises a wireless signal receiver, the processor being configured to wirelessly transmit and receive signals from the electronic transceiver module and the at least one speaker or the at least one microphone.

In accordance with an embodiment of the invention, the face mask covers half the face of the user.

In accordance with an embodiment of the invention, the decorative skin covers all of the user's face, with two eye lenses for the user.

In accordance with an embodiment of the invention, the eye lenses are selected from a group consisting of prescription lenses, tinted lenses, and tinted prescription lenses.

In accordance with an embodiment of the invention, the connection piece comprises an elastic expanding and retracting area such that a desired amount of pressure is achieved such that an air-tight seal against the face of the user is maintained between the face of the user and the respirator.

In accordance with an embodiment of the invention, the decorative skin covers the user's entire head like a helmet and forms a seal around a neck of the user.

In accordance with an embodiment of the invention, at least one cushion pad is attached to the interior of the face mask.

In accordance with an embodiment of the invention, one or more solar panels are attached to the face mask, providing solar power to the power source.

In accordance with an embodiment of the invention, the electronic transceiver module comprises a Secure Digital card slot, the processor being configured to process the non-transitory computer readable media read from the electronic transceiver module.

In accordance with an embodiment of the invention, the at least one filter is detachable and can be attached to the respirator utilizing at least one filter connection port.

In accordance with an embodiment of the invention, the at least one filter connection port produces an audible clicking sound when the at least one filter has been connected properly to the respirator.

In accordance with an embodiment of the invention, at least one fluid tube is attached to the face mask and an inside of the respirator, allowing the user to consume fluids while wearing the face mask.

In accordance with an embodiment of the invention, at least one fan powered by the power source, is attached to the face mask.

In accordance with an embodiment of the invention, at least one sweat pad is attached to the interior of the face mask to absorb the user's sweat.

In accordance with an embodiment of the invention, a screen is attached to the interior of the face mask, the electronic transceiver module being connected to said screen, the processor being configured to display images graphically.

In accordance with an embodiment of the invention, a camera is attached to the face mask.

In accordance with an embodiment of the invention, the face mask is waterproof.

In accordance with an embodiment of the invention, the face mask comprises a heart rate monitor connected to the electronic transceiver module, the processor being configured to process heart rate data from the heart rate monitor.

In accordance with an embodiment of the invention, a plurality of lights for decorative or visual aid are attached to the face mask, the plurality of lights being powered by the power source.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

In the figures, embodiments are illustrated by way of example. It is to be expressly understood that the description and figures are only for the purpose of illustration and as an aid to understanding.

Figure 1:
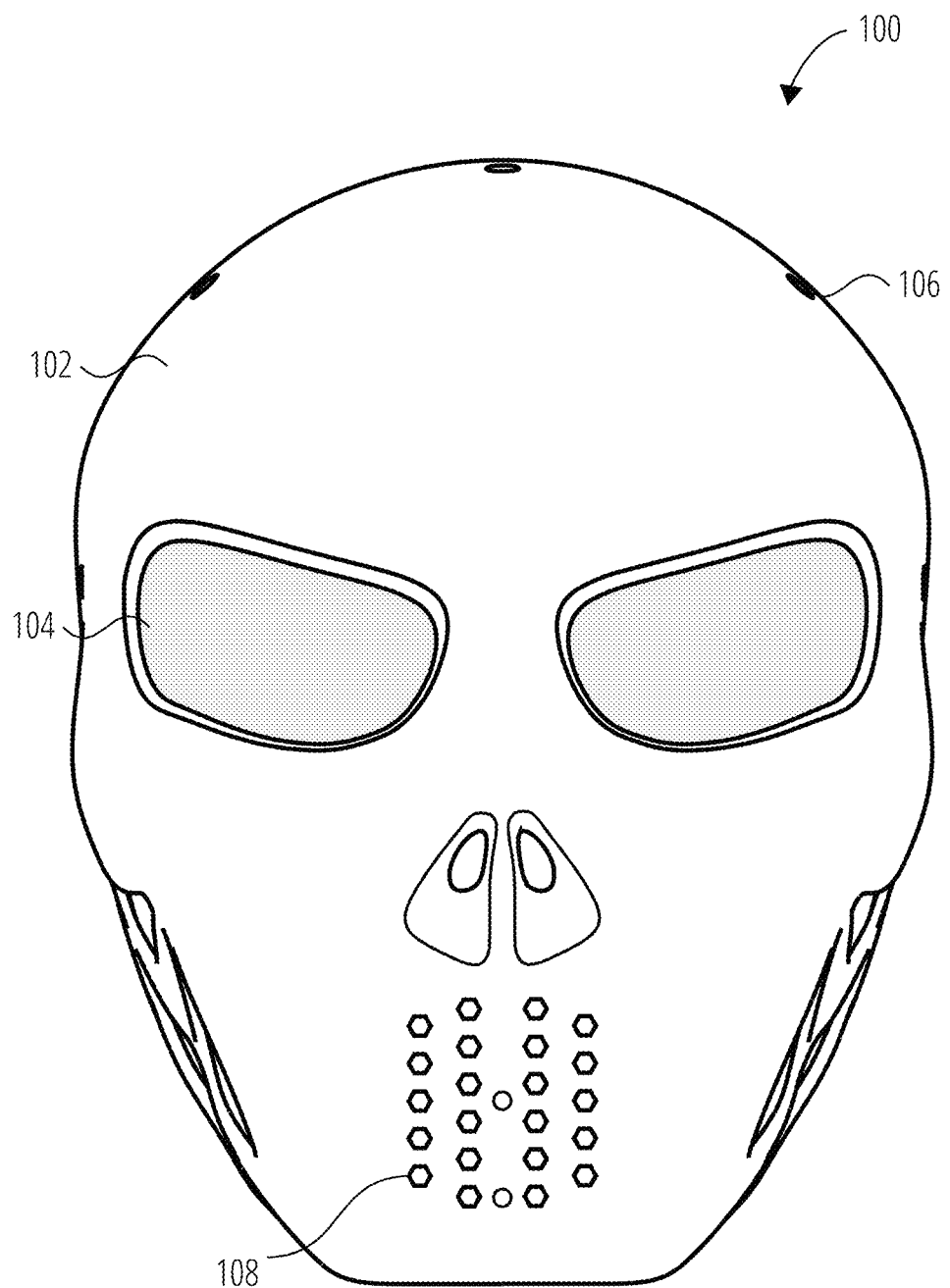

Embodiments will now be described, by way of example only, with reference to the attached figures, wherein the figures:

FIG. 1 illustrates a front view of an example decorative face mask, according to some embodiments.

Figure 2:
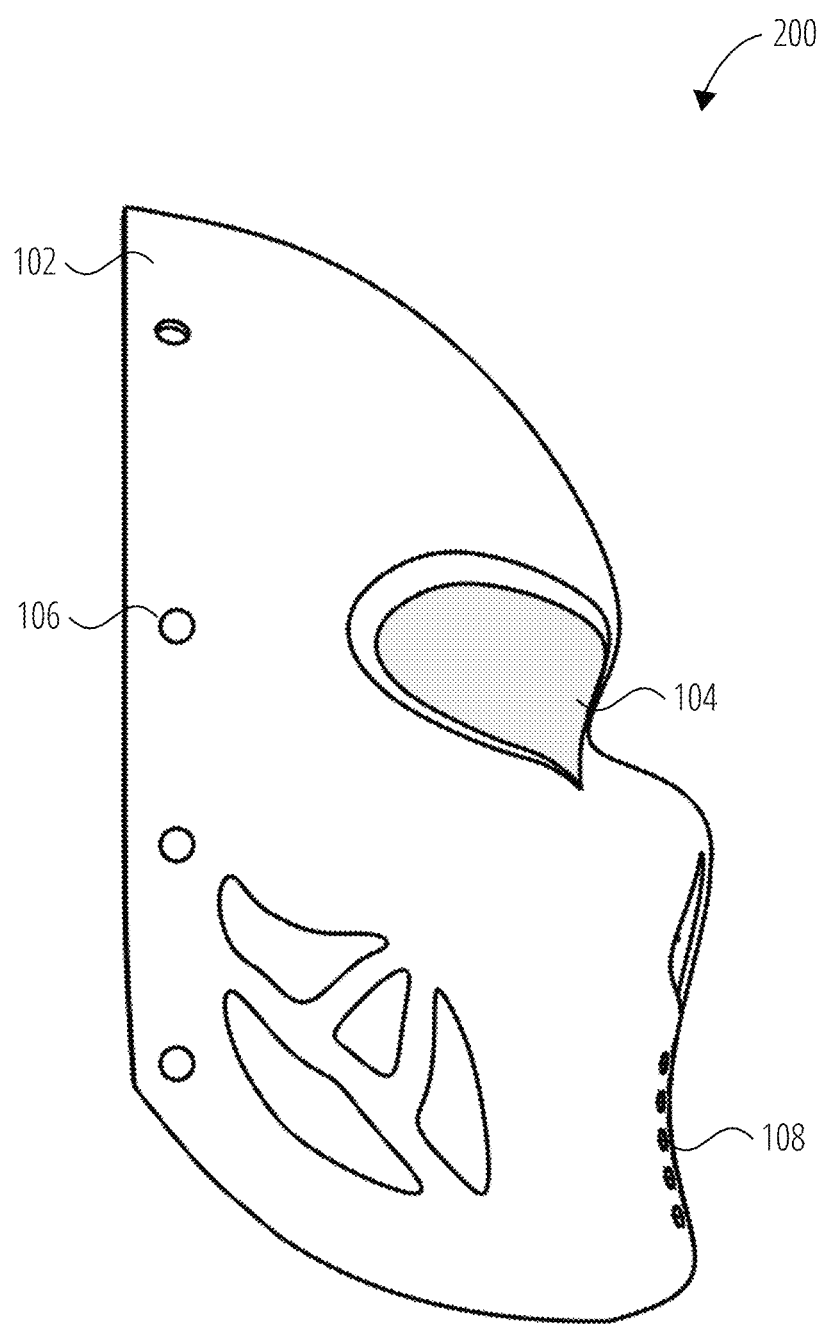

FIG. 2 illustrates a side view of an example decorative face mask, according to some embodiments.

Figure 3:
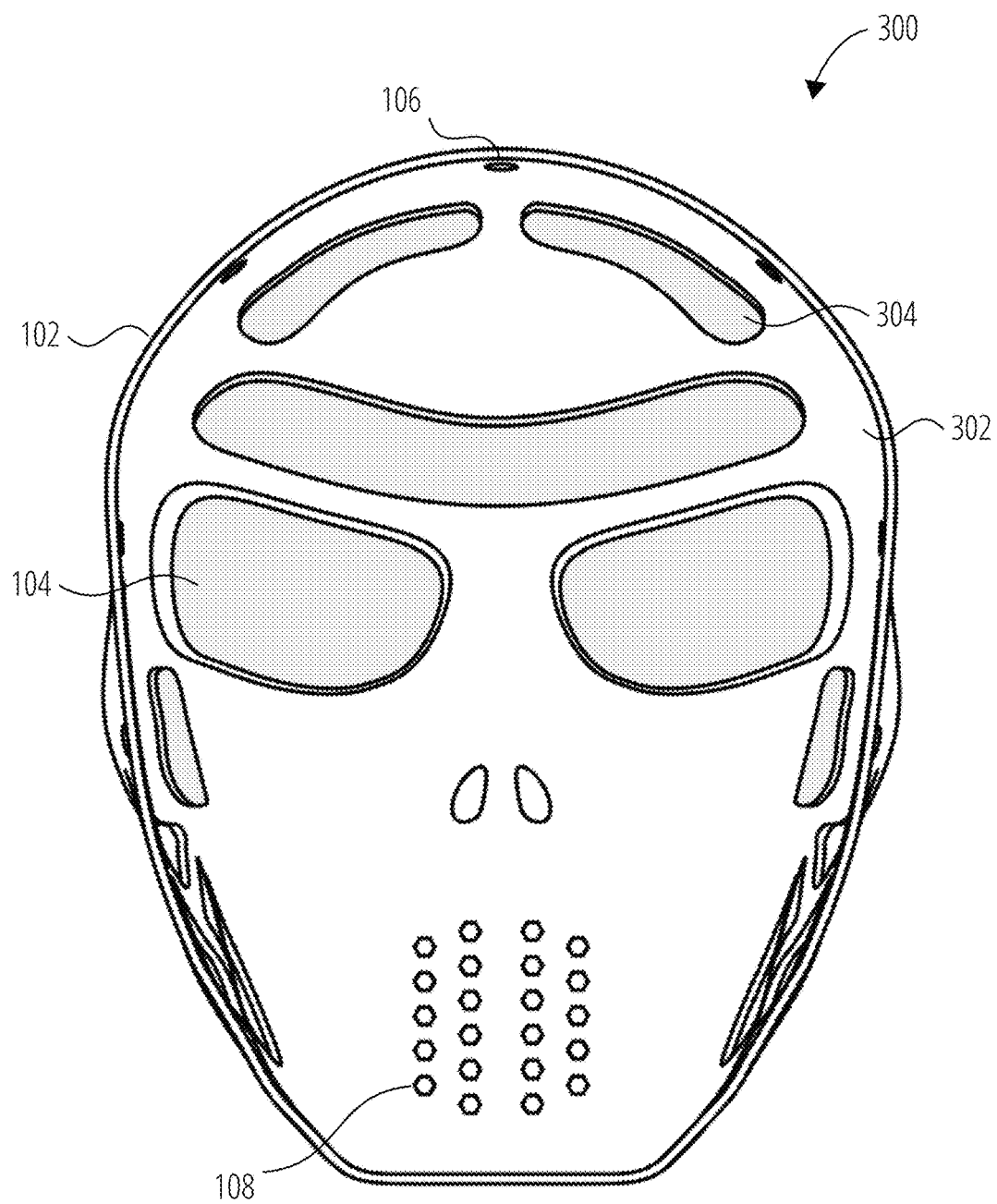

FIG. 3 illustrates a back view of an example decorative face mask, according to some embodiments.

Figure 4:
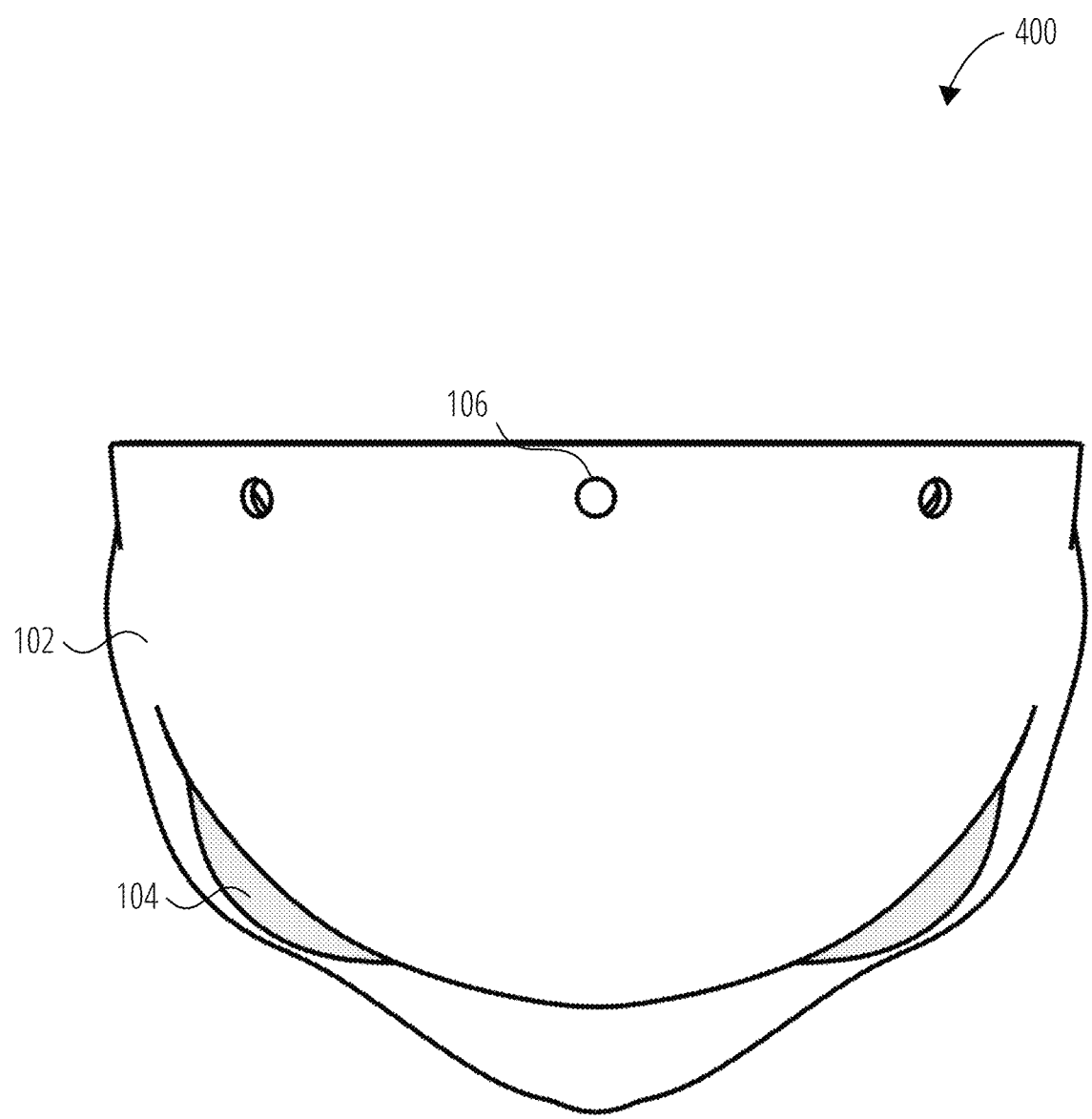

FIG. 4 illustrates a top view of an example decorative face mask, according to some embodiments.

Figure 5:
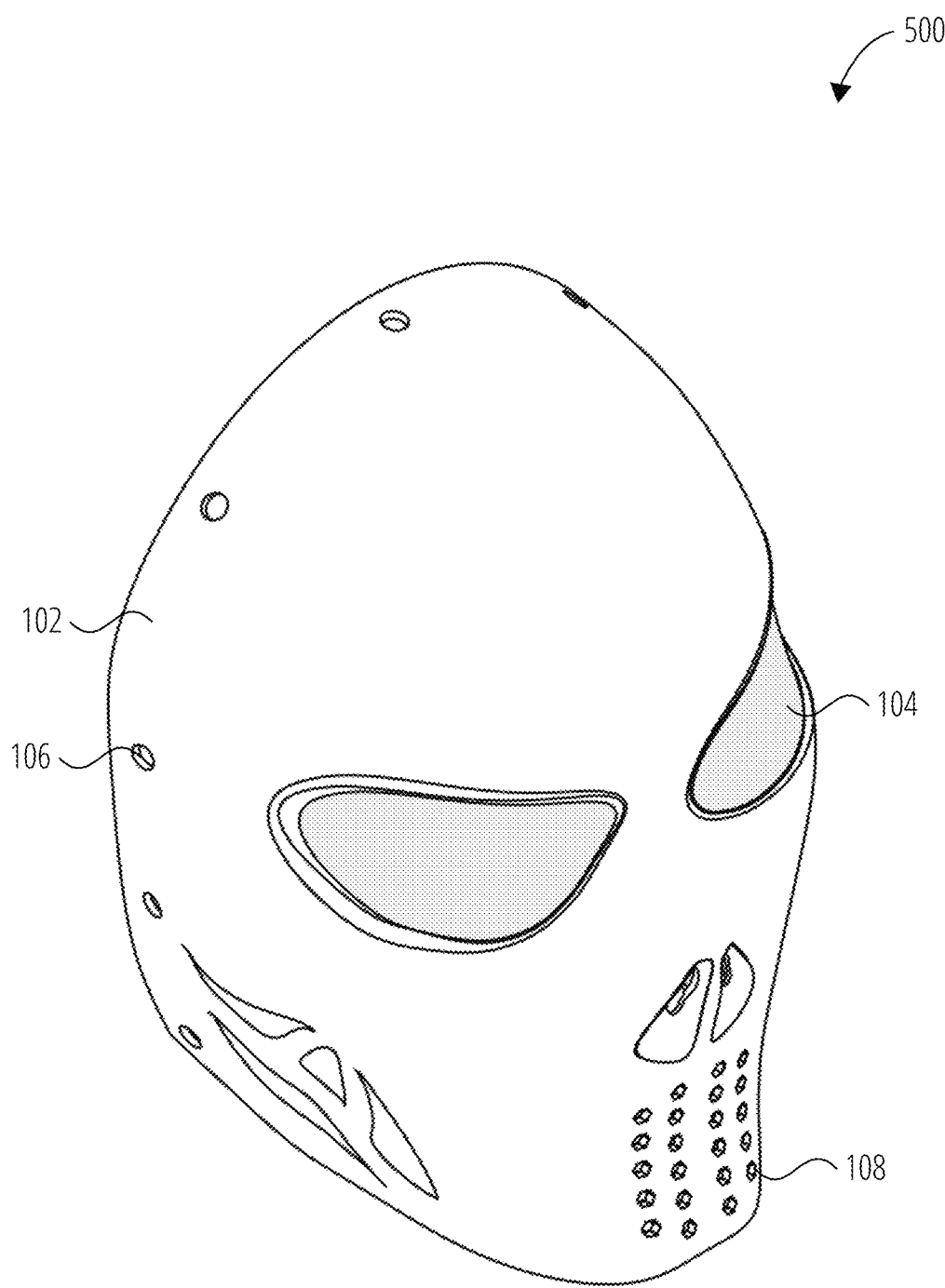

FIG. 5 illustrates a perspective view of an example decorative face mask, according to some embodiments.

Figure 6:
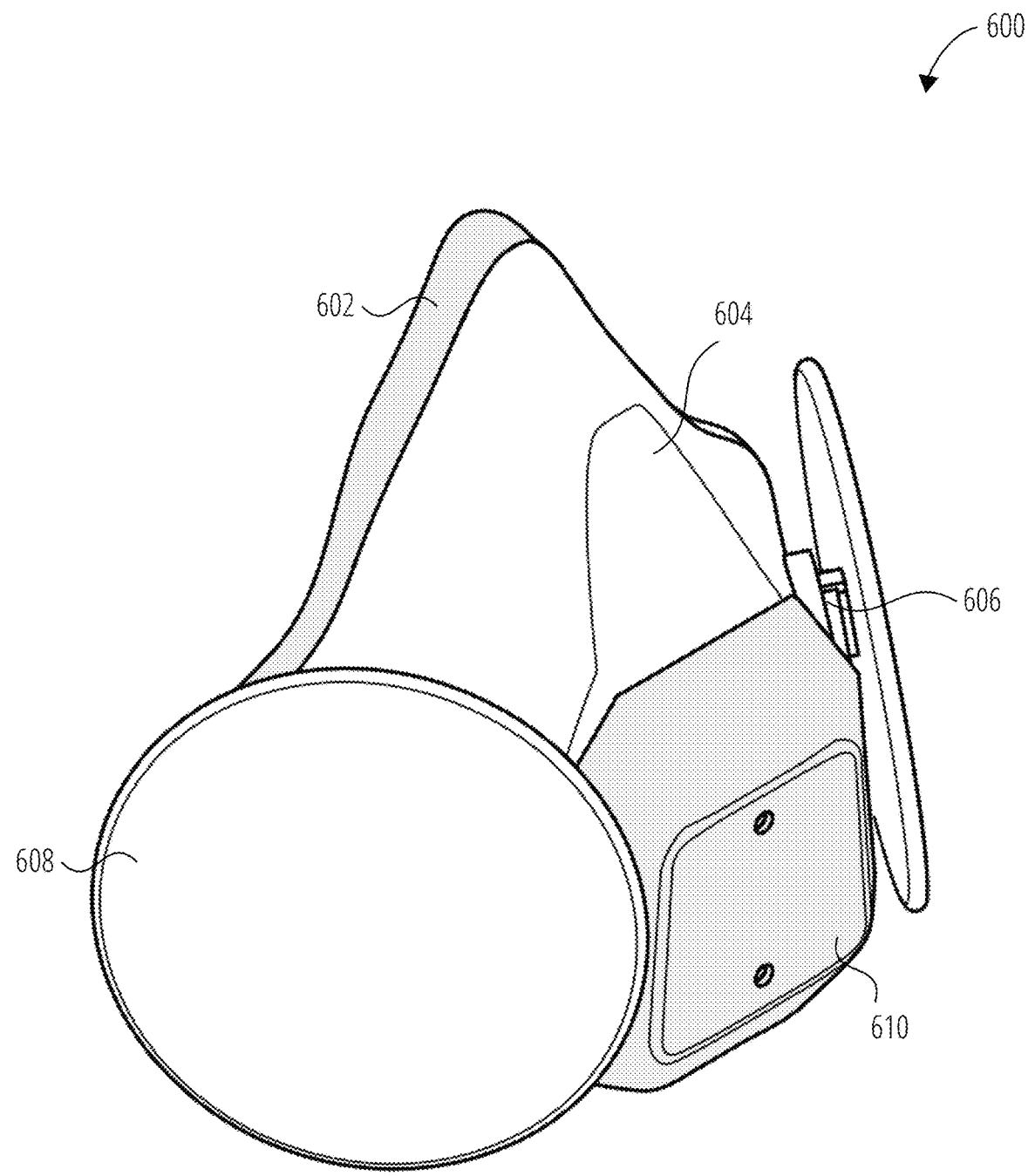

FIG. 6 illustrates a perspective view of an example respirator, according to some embodiments.

Figure 7:
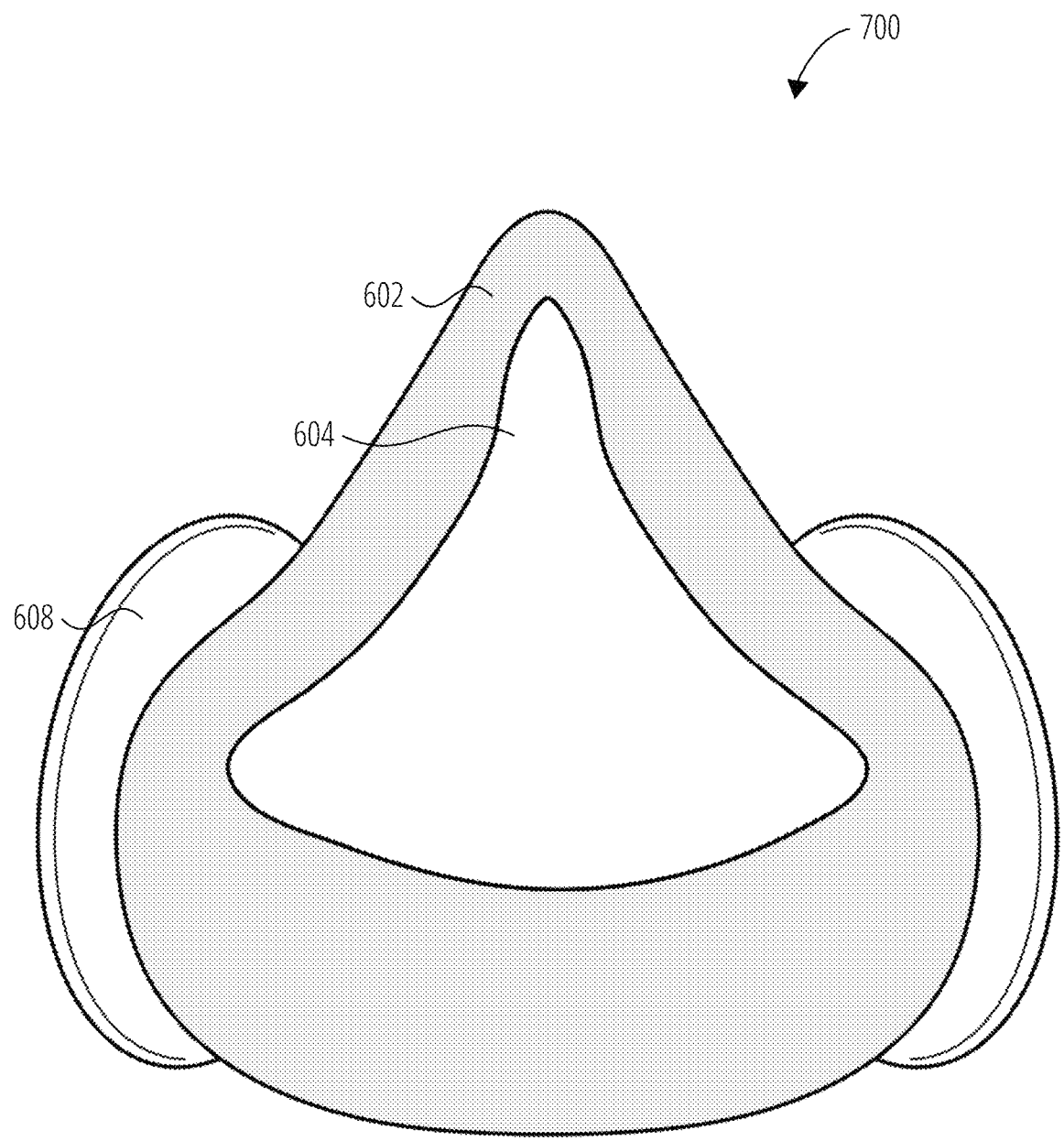

FIG. 7 illustrates a back view of an example respirator, according to some embodiments.

Figure 8:
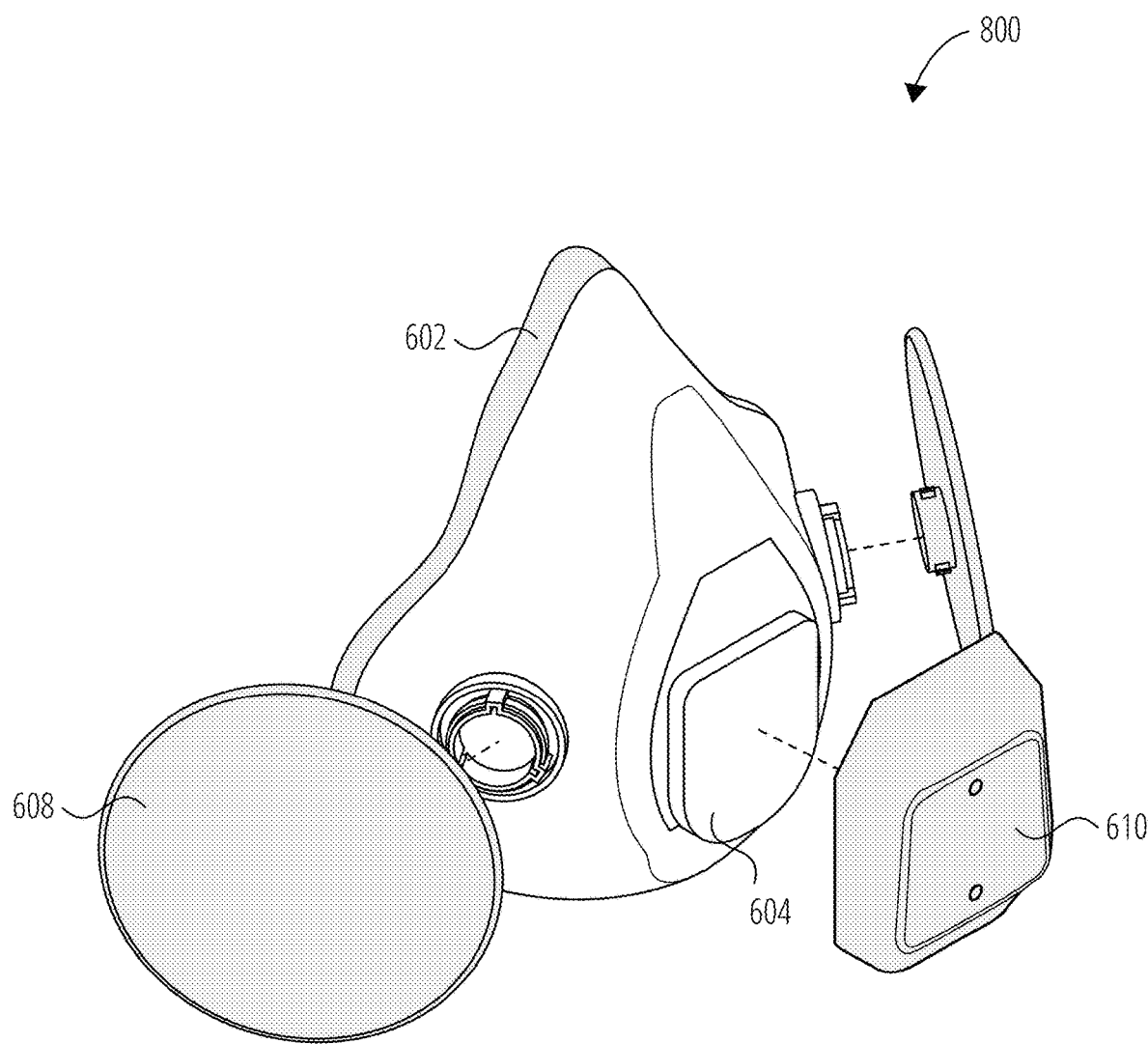

FIG. 8 illustrates an exploded view of an example respirator, according to some embodiments.

Figure 9:
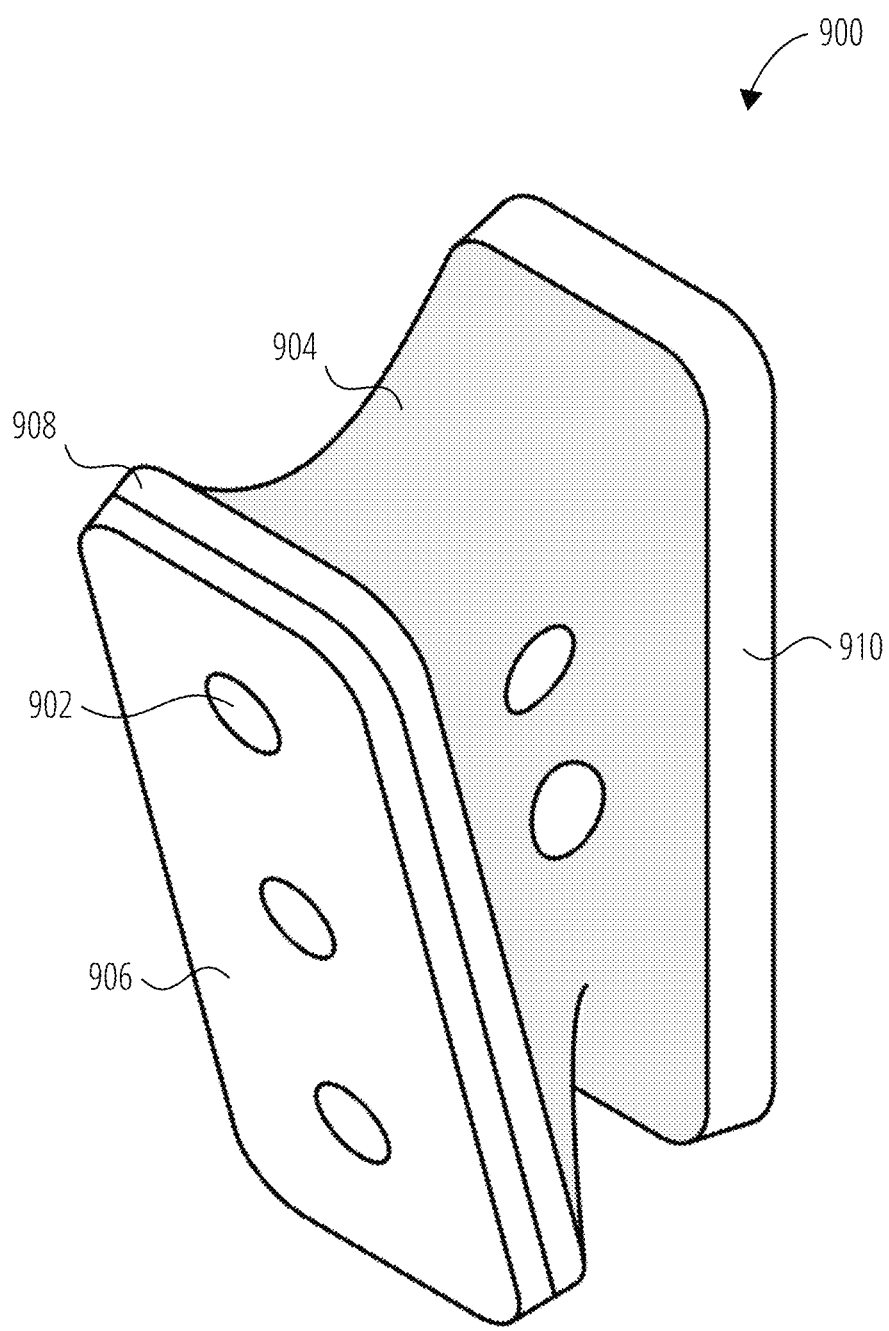

FIG. 9 illustrates a perspective view of an example connection piece, according to some embodiments.

Figure 10:
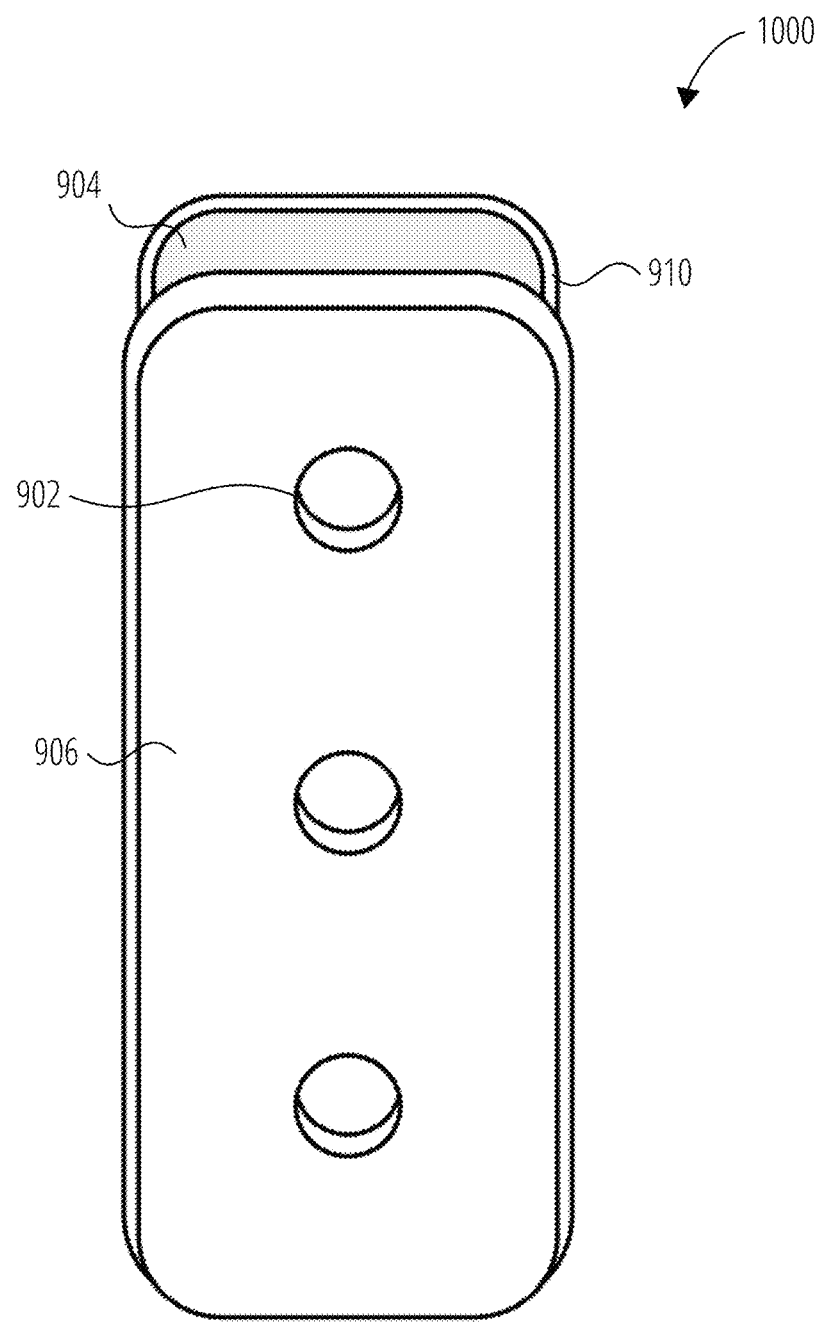

FIG. 10 illustrates a front view of an example connection piece, according to some embodiments.

Figure 11:
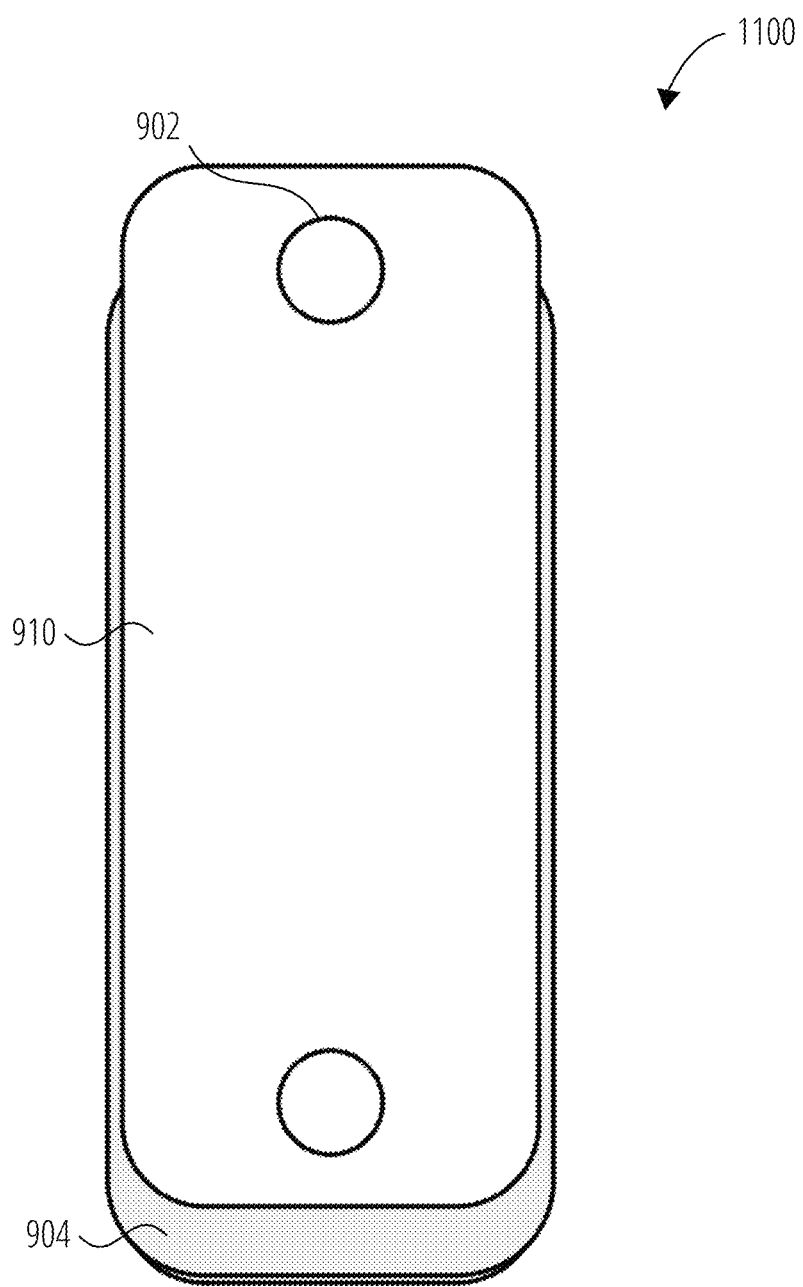

FIG. 11 illustrates a back view of an example connection piece, according to some embodiments.

Figure 12:
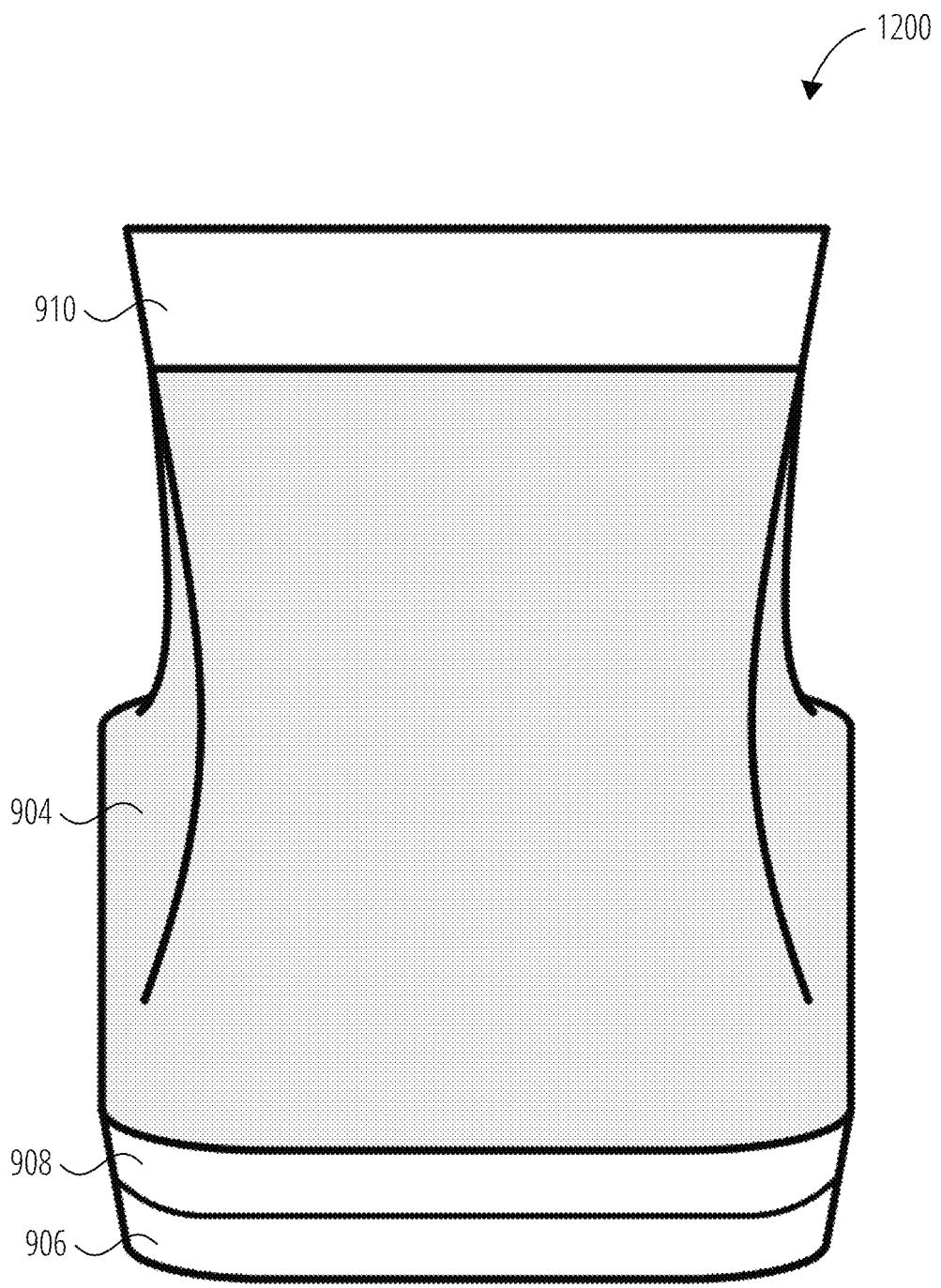

FIG. 12 illustrates a top view of an example connection piece, according to some embodiments.

Figure 13:
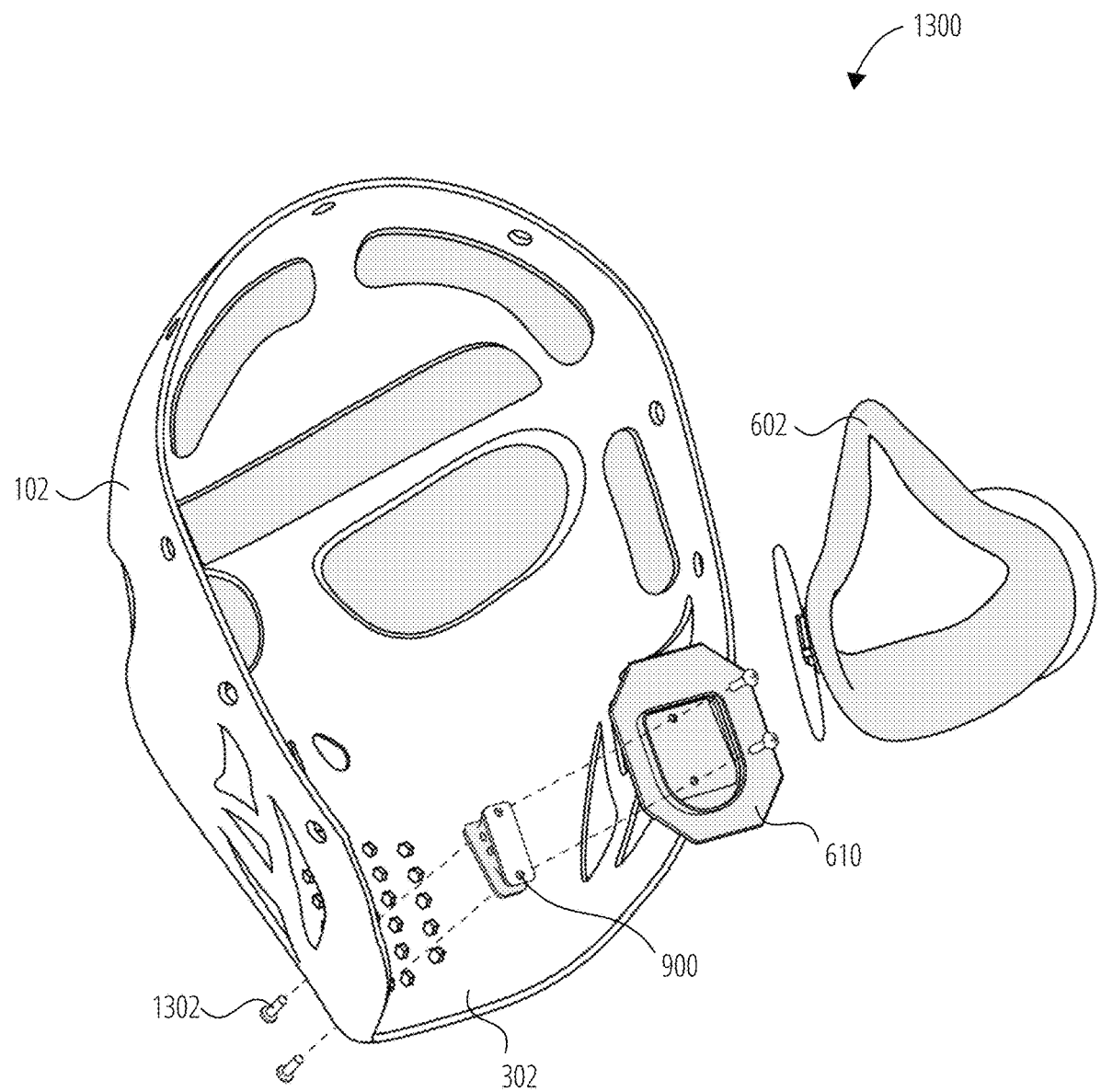

FIG. 13 illustrates an exploded view of an example assembled unit, according to some embodiments.

Figure 14:
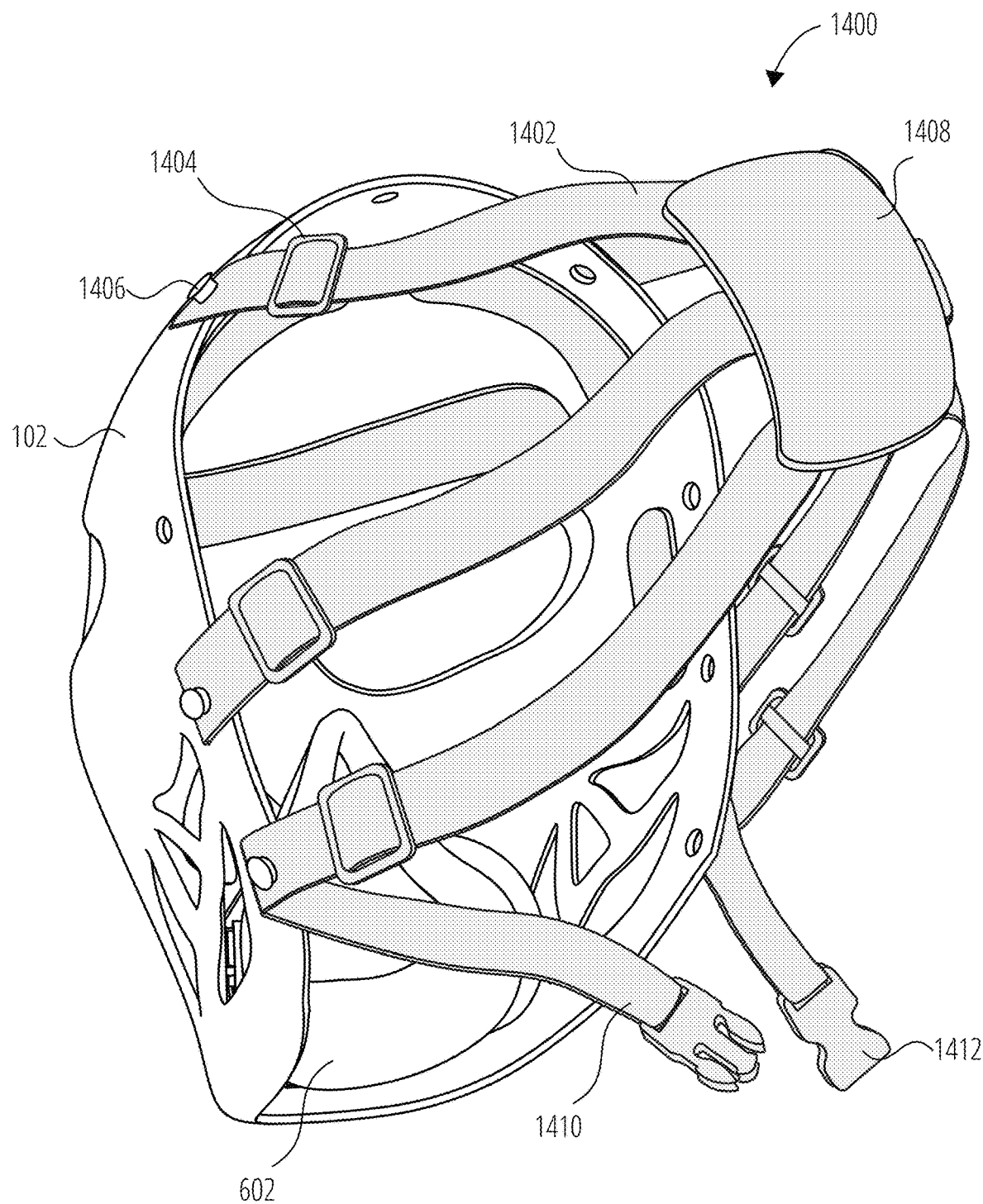

FIG. 14 illustrates a perspective view of an example partially assembled unit, according to some embodiments.

Figure 15:
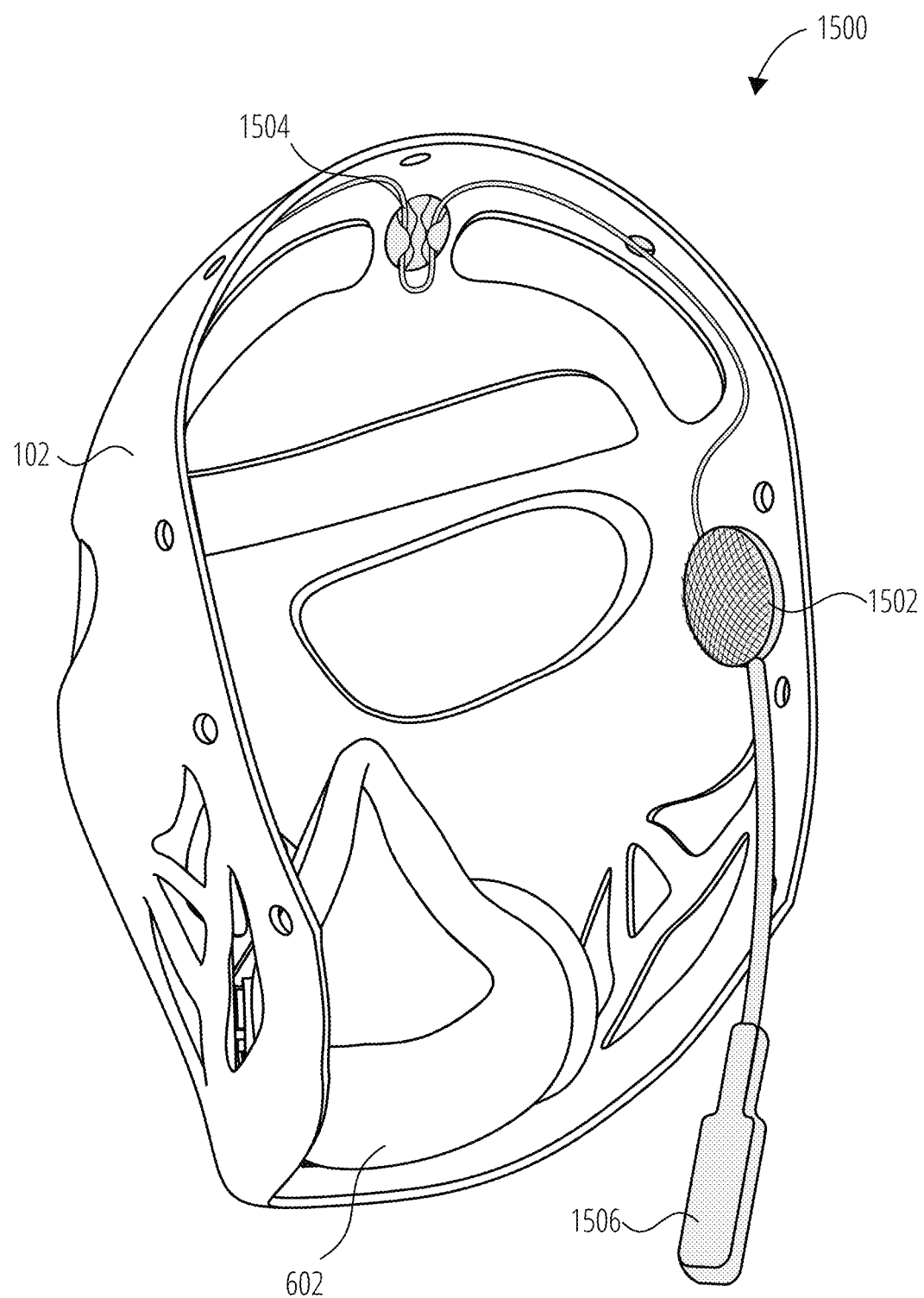

FIG. 15 illustrates a perspective view of an example mask fit, according to some embodiments.

DETAILED DESCRIPTION

The details of one or more embodiments of the subject matter of this specification are set forth in the accompanying drawings and the description below. Other features, aspects, and advantages of the subject matter will become apparent from the description, the drawings, and the claims.

Like reference numbers and designations in the various drawings indicate like elements.

The present invention describes a decorative respirator and communication mask that overcomes disadvantages inherent in the existing respirator and face mask apparatuses. The present invention provides an equally protective face mask that may be attractive and stylish in appearance and may provide additional benefit to the user through speakers and a microphone, among other benefits. As such, the general purpose of the present invention, which will be described subsequently in greater detail, is to provide a new and improved respirator which provides the advantages and overcomes the aforementioned disadvantages.

A face mask, decorative appearance and communication device for a user, is presented herein. The face mask comprises a decorative skin, having at least one strap attached to an outer perimeter of the decorative skin, a respirator which utilizes at least one filter, the respirator being attached to a connection piece, and the connection piece being attached to the decorative skin. The face mask further comprises at least one speaker and at least one microphone mounted to an interior of the face mask, an electronic transceiver module attached to the face mask and a power source attached to the face mask. The at least one strap secures the face mask to a head of the user. The at least one filter is connected to the respirator, the respirator forming an air-tight seal with a face of the user. The power source powers the at least one speaker, the at least one microphone, and the electronic transceiver module. The electronic transceiver module comprises a processor coupled to a computer memory and non-transitory computer readable media, the processor configured to transmit and receive signals from the electronic transceiver module and the at least one speaker or the at least one microphone.

In some embodiments, the electronic transceiver module comprises a wireless signal receiver, the processor being configured to wirelessly transmit and receive signals from the electronic transceiver module and the at least one speaker or the at least one microphone.

FIG. 1 provides a front view 1000 of an example decorative face mask, according to some embodiments. Face mask skin 102 may be decoratively colored. For example, in some embodiments, it may be patterned with a camouflage design. In some embodiments the face mask may glow in the dark. In alternate embodiments face mask skin 102 may be formed from different materials, such as plastic, wood, metal, aluminum, among others.

Face mask skin 102 may, in alternate embodiments, have a different overall shape. For example, the design of the mask may be modeled after a superhero's mask, a famous person, a video game character, a princess, among others.

Eye lenses 104 may allow for a user's vision to not be obstructed when wearing face mask skin 102. In some embodiments, eye lenses 104 may be non-tinted, clear lenses, and in others they may be shaded. In some embodiments eye lenses 104 may use prescription lenses. The shape of eye lenses 104 may vary depending on the design of face mask skin 102. For example, face mask skin 102 may be designed to look like a particular superhero and eye lenses 104 may be shaped accordingly to fit this design, in some embodiments. In some embodiments, the eye lenses 104 are selected from a group the group consisting of prescription lenses, tinted lenses, and tinted prescription lenses.

Face mask skin 102 may have strap attachment connections 106, which may provide a location to connect any attachments such as straps. Vent holes 108 may provide breathability, and the size, shape, and location may vary in some embodiments, depending on the design of face mask skin 102.

FIG. 2 provides a side view 200 of an example decorative face mask skin 102, according to some embodiments. In this view, eye lenses 104, strap attachment connections 106, and vent holes 108 can also be seen.

FIG. 3 provides a back view 300 of an example decorative face mask skin 102, according to some embodiments. Once again, in this view eye lenses 104, strap attachment connections 106, and vent holes 108 can be seen.

An inside 302 of face mask skin 102 can also be seen. In some embodiments, inside 302 may be made from a different material than face mask skin 102. For example, in some embodiments, inside 302 may be felt or a hook-and-loop fastener material, such as Velcro, among others. In some embodiments, a hook-and-loop fastener inside 302 may provide easy adjustment of attachments connected to strap attachment connections 106.

Cushion pads 304 may be easily adjustable face pads. In some embodiments, cushion pads 304 may provide the user of face mask skin 102 additional comfort, and in some embodiments, may provide additional benefit such as sweat retention, better fit of face mask skin 102, among others. In some embodiments, at least one sweat pad is attached to the interior of the face mask to absorb the user's sweat.

FIG. 4 provides a top view 400 of an example decorative face mask skin 102, according to some embodiments. In this view, eye lenses 104 and strap attachment connections 106 can be seen.

FIG. 5 provides a perspective view 500 of an example decorative face mask skin 102, according to some embodiments. Once again, in this view eye lenses 104, strap attachment connections 106, and vent holes 108 can be seen.

FIG. 6 provides a perspective view 600 of an example respirator, according to some embodiments. A respirator half face mask 602 may be made of rubber, or a similar material, and conforms to the user's face to create a tight seal. Front mounting bracket 604 provides support to the respirator half face mask 602 and may be made from a harder material than rubber respirator half face mask 602.

In some embodiments, the respirator half face mask 602 may have filter connection ports 606. Filter connection ports 606 may be the standard shape and dimension, which may allow multiple different filter types, by various manufacturers to be attached. In other embodiments, filter connection ports 606 may have the ability to conform with other tube attachments from other manufacturers, or other additional attachments. For example, drinking tubes to carry a beverage to the user of face mask skin 102, or oxygen tubes to provide oxygen to the user may be attached to the filter connection ports 606, in some embodiments. In other embodiments, the respirator half face mask 602 may include a condensation drip valve.

Filters 608 may be a simple attachment piece to a respirator half face masks 602 connected to the filter connection ports 606 and may be easy for everyone to use. For instance, installation of filters 608 may be done by children, and seniors. In some embodiments, connecting filters 608 to the filter connection ports 606 may provide an audible click, or some form of confirmation that the filter connection ports 606 has been connected properly. This additional confirmation of proper connection to filter connection ports 606, in some embodiments, may further increase the ease of use for everyone. As a non-limiting example, in some embodiments filters 608 may be N95 or P100 filters. In other embodiments, filters 608 may be more specialized filters for airborne gasses, extra fine particulates, among others.

Connection plate 610 may, in some embodiments, provide the main mounting area for connection piece 900. In some embodiments, connection plate 610 may act as an exhale vent.

The respirator half face mask 602 may be a uniform shape to fit most human faces, to provide the tight seal and comfort for the user, as described above. In some embodiments, the respirator half face mask 602 may be a custom shape fit the individual shape of the user's face.

FIG. 7 provides a back view 700 of an example respirator, according to some embodiments. Respirator half face mask 602 can be seen from the back and shows the shape which may easily conform the user's face, creating a tight seal. A front mounting bracket 604 can also be seen from the back, as well as respirator half face masks 602.

FIG. 8 provides an exploded view 800 of an example respirator, according to some embodiments. This figure provides a clear view of respirator half face mask 602. In some embodiments, filters 608 may be attached to a respirator half face mask 602 by being connected to the filter connection ports 606. Connection plate 610, in some embodiments, may be attached to respirator half face mask 602, sitting on top of a front mounting bracket 604.

FIG. 9 provides a perspective view of an example connection piece 900, according to some embodiments. Connection piece 900 may have pre-milled screw holes 902 which can provide an attachment location for connection piece 900 to the face mask skin 102 and the respirator half face mask 602.

Connection piece 900 may contain an expanding/retracting area 904. The expanding/retracting area 904 may, in some embodiments, be made out of a spongey, elastic, rubbery, among others, material that may be designed such that it maintains the appropriate amount of pressure on the user's face, creating an air-tight seal while not being discomforting.

To attach connection piece 900 to face mask skin 102, in some embodiments, an attachment plate 906 may be used. Attachment plate 906 may be a softer material to allow it to better conform to the respirator and allow for a better air-tight seal to be created. In some embodiments, a retaining piece 908 may be used in between connection piece 900 and attachment plate 906. Retaining piece 908 may be made from a durable material and would provide support between the respirator half face mask 602 and the face mask skin 102. In some embodiments, retaining piece 908 may have a detachable clip location, which may allow for quick and easy changing of the respirator half face masks 602 and respirator half face mask 602.

To attach connection piece 900 to respirator half face mask 602, in some embodiments, an attachment plate 910 may be used. Attachment plate 910 may be made of a spongey material to conform to a variation of different masks. In some embodiments, there may be a harder material between expanding/retracting area 904 and attachment plate 910 to increase durability. In some embodiments, the connection piece 900 comprises an elastic expanding and retracting area such that a desired amount of pressure is achieved such that an air-tight seal against the face of the user is maintained between the face of the user and the respirator.

FIG. 10 provides a front view 1000 of an example connection piece 900, according to some embodiments. Front view 100 provides a better view of attachment plate 906 and pre-milled screw holes 902. Expanding/retracting area 904 and attachment plate 910 can also be seen, which may, in some embodiments, comprise connection piece 900.

FIG. 11 provides a back view 1100 of an example connection piece 900, according to some embodiments. Back view 1100 provides a better view of attachment plate 910, and also shows pre-milled screw holes 902, and expanding/retracting area 904.

FIG. 12 provides a top view 1200 of an example connection piece 900, according to some embodiments. In this embodiment, both attachment plate 906 and attachment plate 910 can be seen, as well as expanding/retracting area 904 and retaining piece 908.

FIG. 13 illustrates an exploded view 1300 of an example assembled unit, according to some embodiments. Screws 1302 may be used to secure connection piece 900 to an inside 302 of face mask skin 102, connection piece 900 being connected with screws 1302 to connection plate 610 which is attached to a respirator half face mask 602, in some embodiments.

FIG. 14 provides a perspective view of an example partially assembled mask 1400, according to some embodiments. Straps 1402 may be used to attach face mask skin 102 securely to the head of the user. Straps 1402 may be made from traditional canvas, leather, or fabric straps, among others. In some embodiments, the straps 1402 may have elastic properties, that allow for more comfort, easier adjustment, and may aid in maintaining a proper seal of the respirator half face mask 602 on the face of the user. In alternate embodiments, the straps 1402 may have the ability to have add-on connections. For instance, in an example embodiment, straps 1402 may be connected to a nylon sock material, or an insulated winter cap material, among other add-on connections.

In some embodiments, the straps 1402 may have strap adjusters 1404 which may further help in providing a secure fit to the head of the user. Straps 1402 may be connected to a face mask skin 102 using strap mask connectors 1406. Strap mask connectors 1406 may vary in the amount of connecting and adjustable items, such as simple as a hook and hole, a button, an adjustable belt clip, an adjustable ratcheting belt clip, among others. In some embodiments, the straps 1402 may be designed to allow for the mask to rest on top of the head of the user easily, for example, if the user needed to take the mask off quickly for a moment.

Straps 1402 may be secured behind the head of the user, in some embodiments, with a back strap connector 1408. Back strap connector 1408 may act as a uniform connection point for some, many, or all mask straps 1402. In some embodiments back strap connector 1408 may have other attachment connections for other add-on pieces. For example, in alternate embodiments, there may be a simple clip on the back strap connector 1408, such that when the mask is not in use, it could be hung up, on a bag, backpack, purse, belt, or coat hook, among others. In other embodiments, there may be a ratcheting tightening bracket, similar to those found in a hard hat, which may further provide better comfort, more secure fit, and a tighter seal with a respirator half face mask 602.

In some embodiments, the respirator half face mask 602 may potentially require an additional respirator strap 1410 around the back of the neck of the user. Respirator strap 1410 may be secured behind the neck of the user with a respirator strap clip 1412.

FIG. 15 provides a perspective view of an example mask 1500, according to some embodiments. Mask 1500 may have one or more speakers 1502. In alternate embodiments speakers 1502 may be earphones. In some embodiments, speakers 1502 may be connected to a central computer 1504. In some embodiments, speakers 1502 may have wireless connection ability, such as Bluetooth®, and may connect to a user's electronic device. For example, the user of mask 1500 may want to listen to music through speakers 1502 and could connect wirelessly through Bluetooth® to their phone. In some embodiments, mask 1500 may have external speakers, so that those other than a user of the mask may hear what may be playing.

In some embodiments, mask 1500 may have a microphone 1506, which similar to speakers 1502, may be connected to a central computer 1504, and in some embodiments may have wireless connection ability. In alternate embodiments, microphone 1506 may be an internal microphone, attached to the inside 302 of face mask skin 102. Conversely, in other embodiments, microphone 1506 may be a simple external microphone. In some embodiments, microphone 1506 may be moisture resistant. In some embodiments, central computer 1504 may include a power source, such as, a battery pack.

Central computer 1504 may act as a central connection hub for the various electronic components of mask 1500, such as speakers 1502 and microphone 1506, and in some embodiments, may provide other electronic features via wired or wireless connection. In some embodiments, central computer 1504 may have connection ports to allow wired to connection to other electronic devices, for example, plugging in a phone or connect to a vehicle. In other embodiments, central computer 1504 may have an external battery pack, radio, Global Positioning System (GPS), an SD card slot, among others. For an example embodiment, central computer 1504 may have an SD or micro SD slot which a user could upload their music library onto, and plug said SD or micro SD card into the central computer 1504 to listen to their music through speakers 1502. In some embodiments, the electronic transceiver module comprises an SD card slot, the processor being configured to process the non-transitory computer readable media read from the electronic transceiver module.

As a non-limiting example, say John Doe may be wearing mask 1500, and receives a phone call on his cell-phone. John may answer the call on his phone, and because his phone may be wirelessly connected to central computer 1504, John can hear the caller through speakers 1502 and the caller can hear John because he may be speaking into microphone 1506. When John is finished with the call, he may want to listen to music, but he may not have any music locally on his phone. Luckily, John has a micro SD card loaded with all of his favorite songs and can insert the micro SD card in central computer 1504 and listen to his music through speakers 1502 while continuing to wear mask 1500 the entire time.

In some embodiments, a simple application may be created for mask 1500. The application may be run on central computer 1504 and may provide additional functionality. For example, in some embodiments, the app may provide simple connectivity, warranty items, directions, emergency calling, chatting or messaging platform, Walkie-Talkie, games, among others. For example, in a non-illustrative embodiment, central computer 1504 may have a music playing application, which may allow friends to upload different songs to create a unique playlist.

Mask 1500 may, in some embodiments, have special features or add-ons. For instance, in some embodiments, central computer 1504 may be powered and continuously charged by one or more solar panels attached to the mask. In some embodiments, mask 1500 may include an external battery pack, which could act as a larger charging hub able to charge the user's phone, for example. In some embodiments, mask 1500 may be equipped with head lights to help the user see better in dark places or at night. Mask 1500 may also have decorative lights in some embodiments, such as holiday lights during winter festivities. In some embodiments, a plurality of lights for decorative or visual aid are attached to the mask 1500, the plurality of lights being powered by the power source.

In some embodiments, mask 1500 may have a drinking tube attached. For example, this could be an additional component attached to the side of respirator half face mask 602, and a tube may pass through the side of the respirator, or one of the filter connection ports 606 which could carry water or any drink to the user. In some embodiments this drink tube may contain a non-drip sucker on the inside of respirator half face mask 602, which may be pulled over to the user's mouth using their tongue, and when the user is finished drinking from the sucker may retract and not drip. This add-on may be convenient to a user working in a hot environment for example, who may want to keep their respirator and mask on but would still like to be able to take a drink of water. Further, in some embodiments, mask 1500 may have fans, such as cooling fans which may provide better air circulation inside the mask.

In some embodiments, mask 1500 may have a smoking tube attached, which may allow the user to use a cigarette, a cigar, a vape, among others. Similar to a drinking tube, in some embodiments, a smoking tube may be pass through the side of respirator half face mask 602 or through one of the filter connection ports 606. In some embodiments, a single fluid tube may be attached to mask 1500, passing through the side of respirator half face mask 602 or through one filter connection ports 606, which may allow a user to consume fluids, such as smoking, oxygen, water, among others. In some embodiments, the at least one filter connection port 606 produces an audible clicking sound when the at least one filter 608 has been connected properly to the respirator.

In some embodiments, mask 1500 may have sweat collecting pads to collect sweat and avoid sweat dripping on the user's face and may have a sweat draining tube which may drain the user's sweat out of the mask. In some embodiments, mask 1500 may have a heart rate monitor, blood tester, or other health related monitors attached. In some embodiments, the face mask comprises a heart rate monitor connected to the electronic transceiver module, the processor being configured to process heart rate data from the heart rate monitor.

In alternate embodiments, respirator half face mask 602 may be replaced with a tube connection, which may allow for connection to more sophisticated filters, or an oxygen device. For example, in some embodiments, an external filter which may last longer and/or may provide better filtration may be attached to the side of straps 1402, or onto the user's back.

In some embodiments, mask 1500 may have an antenna, which may be used for Walkie-Talkie connection, AM or FM radio, satellite radio, among others. In some embodiments, a screen may be mounted on an inside 302, and may connect to an electronic device, such as a phone, tablet, smartwatch, among others. This add-on may allow for the user to see incoming messages, who is calling, or the time, for example. Said screen may also allow for display of information related to other electronic devices connected to central computer 1504. For example, in some embodiments, said screen may display speed, step counter, heart rate, blood sugar level, battery power level, among others. In some embodiments, said screen may be a heads-up display, which may allow the user to take advantage of augmented reality. For example, a user may be able to see both the road and directions through eye lenses 104 on said screen. In alternate embodiments, a screen may provide additional features such as, but not limited to, tinting features, a reverse display, wireless connection strengths, and others. For instance, in some embodiments, mask 1500 may have a reverse display screen which may allow the user to see through eye lenses 104 clearly while others may see a different image on the reverse display screen, such as different colored eyes, or superhero eyes, among others. In some embodiments, a screen is attached to the interior of the face mask, the electronic transceiver module being connected to said screen, the processor being configured to display images graphically.

In some embodiments, mask 1500 may have a face plate or face shield, which may, dependent on the design, be spring loaded, clicking into place and retracting at a touch of a button. In alternate embodiments, a camera unit may be connected to central computer 1504 and may be attached to mask 1500. In some embodiments, mask 1500 may be fitted to provide the appropriate protection required for a safety helmet for various activities, such as, skateboard, bike, scooter, roller blades, horse riding, machine operation, motorcycle, All-Terrain Vehicle (ATV) riding, Sea-Doo®, Ski-Doo®, Argo®, among others. In alternate embodiments, mask 1500 may be water-resistant and/or waterproof, such that mask 1500 would not fail if a user is caught in rain or submerged in water.

In alternate embodiments, mask 1500 may be shaped like a helmet. In some embodiments mask 1500 may be equipped with a solar panel to charge the battery pack in central computer 1504. Similar to face mask skin 102, said helmet may also be customized with unique designs, such as glow in the dark, camouflage, plaid, among others. Said helmet may be made out of different materials, such as plastic, wood, metal, aluminum, among others in some embodiments. For example, mask 1500 may be shaped like a helmet and made with the proper material and design to resemble a superhero.

In some embodiments, mask 1500 may be equipped with an air conditioning unit, which may keep the internal atmosphere within a helmet mask 1500, for example, at a user's desired temperature. In some embodiments, mask 1500 may be a helmet form factor, and central computer 1504 may be connected to a mounted screen which may display a break or connection line, indicating the rough location of where it may be safe for the user to remove a helmet.

In some embodiments, mask 1500 may have latches. In some embodiments said latches may be on straps 1402, or a part of strap adjusters 1404.

In some embodiments, particularly those where mask 1500 is in a helmet form factor, a neck connection pad may be worn by a user. Said neck connection pad may worn by a user, and may provide an air-tight, comfortable seal. In some embodiments, said neck connection pad may also include straps 1402 to attach comfortably and securely to a user. In some embodiments, mask 1500 may have exhaust ports which may allow relief of negative pressure buildup.

The foregoing descriptions of specific embodiments of the present invention have been presented for purposes of illustration and description. They are not intended to be exhaustive or to limit the invention and method of use to the precise forms disclosed. Obviously, many modifications and variations are possible in light of the above teaching. As can be understood, the examples described above are intended to be exemplary only.

The embodiments described were chosen and described in order to best explain the principles of the invention and its practical application, and to thereby enable others skilled in the art to best utilize the invention and various embodiments with various modifications as are suited to the particular use contemplated. It is understood that various omissions or substitutions of equivalents are contemplated as circumstance may suggest or render expedient but is intended to cover the application or implementation without departing from the spirit or scope of the claims of the present invention.

The term "connected" or "coupled to" may include both direct coupling (in which two elements that are coupled to each other contact each other) and indirect coupling (in which at least one additional element is located between the two elements).

As one of ordinary skill in the art will readily appreciate from the disclosure, processes, machines, manufacture, compositions of matter, means, methods, or steps, presently existing or later to be developed, the perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A face mask, decorative appearance and communication device for a user, comprising:
    a decorative skin comprising:
        a face member having an eye lens;
        a plurality of holes disposed on a mouth region;
        a cushion pad configured to interface with a forehead of the user;
        at least one strap attached to an outer perimeter of the decorative skin;
    a respirator comprising a half mask facepiece disposed on an interior side of the decorative skin, wherein the half mask facepiece is configured to enclose a nose and mouth of the user;
    a connection piece adapted to selectively fasten the respirator to the decorative skin, wherein the connection piece comprises an elastic expanding and retracting area configured to maintain a desired amount of pressure between the user and the respirator to form an air-tight seal against the face of the user;

wherein the elastic expanding and retracting area is disposed between a first mounting face and a second mounting face, wherein the first attachment plate is configured to engage with the plurality of holes and the second attachment plate is configured to engage with the half mask facepiece of the respirator;

wherein the respirator is entirely disposed on the interior side of the decorative skin when fastened thereto;

at least one speaker and at least one microphone mounted to an interior of the face mask;

an electronic transceiver module attached to the face mask;

a power source attached to the face mask, wherein the power source is configured to power the at least one speaker, the at least one microphone, and the electronic transceiver module;

wherein the electronic transceiver module comprises a processor coupled to a computer memory and non-transitory computer readable media, wherein the processor is configured to transmit and receive signals from the electronic transceiver module and either the at least one speaker or the at least one microphone;

wherein the at least one strap is configured to secure the face mask to a head of the user in a worn position;

wherein at least one filter is connected to the respirator and wherein the respirator is configured to form an air-tight seal with a face of the user in the worn position.

2. The face mask of claim 1, wherein the electronic transceiver module comprises a wireless signal receiver, the processor being configured to wirelessly transmit and receive signals from the electronic transceiver module and the at least one speaker or the at least one microphone.

3. The face mask of claim 1, wherein the decorative skin is configured to cover all of the user's face, with two eye lenses for the user.

4. The face mask of claim 3, wherein the eye lenses are selected from a group the group consisting of prescription lenses, tinted lenses, and tinted prescription lenses.

5. The face mask of claim 1, wherein at least one cushion pad is attached to the interior of the face mask.

6. The face mask of claim 1, wherein one or more solar panels are attached to the face mask, providing solar power to the power source.

7. The face mask of claim 1, wherein the electronic transceiver module comprises an SD card slot, the processor being configured to process the non-transitory computer readable media read from the electronic transceiver module.

8. The face mask of claim 1, wherein the at least one filter is detachable and can be attached to the respirator utilizing at least one filter connection port.

9. The face mask of claim 8, wherein the at least one filter connection port produces an audible clicking sound when the at least one filter has been connected properly to the respirator.

10. The face mask of claim 1, wherein at least one fluid tube is attached to the face mask and an inside of the respirator, allowing the user to consume fluids while wearing the face mask.

11. The face mask of claim 1, wherein at least one fan powered by the power source, is attached to the face mask.

12. The face mask of claim 1, wherein at least one sweat pad is attached to the interior of the face mask to absorb the user's sweat.

13. The face mask of claim 1, wherein a screen is attached to the interior of the face mask, the electronic transceiver module being connected to said screen, the processor being configured to display images graphically.

14. The face mask of claim 1, wherein a camera is attached to the face mask.

15. The face mask of claim 1, wherein the face mask is waterproof.

16. The face mask of claim 1, wherein the face mask comprises a heart rate monitor connected to the electronic transceiver module, the processor being configured to process heart rate data from the heart rate monitor.

17. The face mask of claim 1, wherein a plurality of lights for decorative or visual aid are attached to the face mask, the plurality of lights being powered by the power source.

* * * * *